United States Patent [19]

Fujii et al.

[11] Patent Number: 4,719,213

[45] Date of Patent: Jan. 12, 1988

[54] ANTI-CANCER COMPOSITION FOR DELIVERING 5-FLUOROURACIL

[75] Inventors: Setsuro Fujii, Toyonaka; Norio Unemi; Setsuo Takeda, both of Tokushima, all of Japan

[73] Assignee: Taiho Pharmaceutical Company Limited, Tokyo, Japan

[21] Appl. No.: 901,202

[22] Filed: Aug. 28, 1986

Related U.S. Application Data

[60] Division of Ser. No. 591,459, Mar. 20, 1986, Pat. No. 4,622,325, which is a division of Ser. No. 214,022, Dec. 8, 1980, Pat. No. 4,507,301, which is a continuation-in-part of Ser. No. 15,161, Feb. 26, 1979, Pat. No. 4,328,229, which is a continuation-in-part of Ser. No. 891,343, Mar. 29, 1977, abandoned.

[30] Foreign Application Priority Data

Apr. 5, 1977 [JP] Japan .................... 52-39341
Jan. 10, 1978 [JP] Japan .................... 53-14676

[51] Int. Cl.$^4$ .......................... A61K 31/505
[52] U.S. Cl. ................................. 514/274
[58] Field of Search ........................ 514/274

[56] References Cited

U.S. PATENT DOCUMENTS

| | | | |
|---|---|---|---|
| 4,328,229 | 5/1982 | Fujii et al. | 514/274 |
| 4,371,535 | 2/1983 | Unemi et al. | 514/274 |
| 4,481,203 | 11/1984 | Fujii et al. | 514/274 |
| 4,507,301 | 3/1985 | Fujii et al. | 514/274 |

FOREIGN PATENT DOCUMENTS

| | | | |
|---|---|---|---|
| 55-007231 | 1/1980 | Japan | 514/274 |
| 55-019244 | 2/1980 | Japan | 514/274 |
| 56-099414 | 8/1981 | Japan | 514/274 |

*Primary Examiner*—Jerome D. Goldberg
*Attorney, Agent, or Firm*—Murray and Whisenhunt

[57] ABSTRACT

An anti-cancer composition for delivering a 5-fluorouracil to cancer tissues in a warm-blooded animal, wherein the cancer is a cancer sensitive to 5-fluorouracil. The composition comprises uracil or a pharmaceutically acceptable salt thereof, and a 5-fluorouracil pro drug selected from the group consisting of 1, 3-bis (2-tetrahydrofuryl)-5-fluorouracil and 3-(2-tetrahydrofuryl)-5-fluorouracil in a small amount of about 0.1 to less than 0.1 mole per mole of uracil or salt thereof.

9 Claims, No Drawings

ANTI-CANCER COMPOSITION FOR DELIVERING 5-FLUOROURACIL

CROSS-REFERENCE TO RELATED APPLICATIONS

This application is a divisional application of Ser. No. 591,459 filed Mar. 20, 1986, now U.S. Pat. No. 4,622,325, which is a divisional of Ser. No. 214,022 filed Dec. 8, 1980, now U.S. Pat. No. 4,507,301, which is a continuation-in-part of Ser. No. 15,161 filed Feb. 26, 1979, now U.S. Pat. No. 4,328,229, which is a continuation-in-part of Ser. No. 891,343 filed Mar. 29, 1977, now abandoned.

FIELD OF THE INVENTION

This invention relates to anti-cancer compositions and methods for delivering 5-fluorouracil to cancer tissues in a warm-blooded animal, wherein the cancer is a cancer sensitive to 5-fluorouracil.

BACKGROUND OF THE INVENTION

Extensive research on the chemotherapy of cancers has heretofore been conducted, with the chemotherapy of cancers commenced in the latter half of the 1940's for the control of nucleic acid metabolism. As antimetabolites to nucleic acids, 6-mercaptopurine was synthesized first, followed by the discovery of 5-fluorouracil.

5-fluorouracil was synthesizd by Duschinsky in 1957 and found to have anti-cancer activity by Heidelberger et al. The compound has a wide anti-cancer spectrum range, produces outstanding effects especially on adenocarcinomas and is therefore one of the anti-cancer agents which are most widely used for clinical purposes. Since 5-fluorouracil is typical of antagonists to nucleic acid metabolism, intensive research is still continued on compounds having 5-fluorouracil as the basic skeleton.

In recent years, various excellent anti-cancer compositions have been introduced into use for the chemotherapy of malignant cancers with progressively improved results. Chemotherapeutic effects so far achieved nevertheless still remain temporary and are not always satisfactory in completely inhibiting the proliferation of cancerous tissues and enabling patients to survive a long period of time. The anti-cancer compositions frequently used for clinical purposes at present are predominantly those consisting essentially of a 5-fluorouracil, and various 5-fluorouracils will be developed in the future. However, anti-cancer compositions comprising a compound having a 5-fluorouracil as its skeleton and serving as the active component thereof have both merits and demerits. For example, 5-fluorouracil, although highly effective, has high toxicity and marked side effects. Accordingly, when administered, the compound produces a therapeutic effect and, at the same time, inevitably gives side effects. Further 1-(2-tetrahydrofuryl)-5-fluorouracil, which has relatively lower toxicity and reduced side effects, is said to be slightly inferior in its anti-cancer effect. In view of these situations, it has been expected to develop more advantageous 5-fluorouracils.

On the other hand, research has been conducted to provide increased anti-cancer efficacies by improving the method or mode of administering anti-cancer compositions which are conventionally used. For example, attempts have been made to use a known anti-cancer agent conjointly with another drug with or without anti-cancer activity to thereby achieve an increased therapeutic efficacy with reduced side effects. The known compositions of this type, nevertheless, are not fully effective for the chemotherapy of malignant cancers.

Compounds containing 5-fluorouracil as the skeleton thereof are thought to exhibit an anti-cancer effect when converted to 5-fluorouracil in the living body. It appears that they generally fail to give a high anti-cancer effect because the resulting 5-fluorouracil is promptly metabolized and thereby inactivated. Accordingly it is desired that the 5-fluorouracil in the living body be prevented from inactivation by some expedient, preferably in such a manner that the 5-fluorouracil present in the cancer tissues will remain active, whereas the 5-fluorouracil present in the normal tissues can be inactivated.

We have made extensive investigations for the development of anti-cancer compositions and have found that when uracil, which has no anti-cancer effect, was admixed with a 5-fluorouracil in an amount of 0.02 to 10 moles per mole of the latter, uracil enhanced the anti-cancer effect of the 5-fluorouracil, enabling the composition to achieve a remarkably increased therapeutic index ($LD_{50}/ED_{50}$). Based on this finding, we filed patent applications (including Japanese Patent Applications No. 39341/1977 and No. 14676/1978, as well as U.S. Ser. Nos. 891,343 and 15,161).

With the above composition, a further increase in the proportion of uracil relative to the 5-fluorouracil results in a large dose, which is difficult to administer both physically and physiologically. Furthermore use of an increased proportion of uracil leads to a reduced $LD_{50}$ and higher toxicity. For these reasons, it appeared favorable with filing e.g., U.S. Ser. No. 891,343, to limit the amount of uracil to 10 moles per mole of the 5-fluorouracil.

However, our experiments conducted with the use of compositions containing larger proportions of uracil have revealed that these compositions achieve much higher anti-cancer activity than when no more than 10 moles of uracil is used per mole of the 5-fluorouracil despite the increase in the proportion of the 5-fluorouracil, thus making it possible to give such compositions at a reduced dose. When given to animals for toxicity tests in which the animals were checked for changes in body weight, the compositions were found to have reduced overall toxicity due to the decrease in the proportion of 5-fluorouracil.

Such results are totally inconceivably from conventional anti-cancer compositions since generally there is no anti-cancer agent that would act uniquely to cancer cells only; if effective on cancer, the usual anti-cancer compositions also invariably have side effects, which can be mitigated at a reduced dose, but a reduced efficacy will then result.

SUMMARY OF THE INVENTION

The present invention provides anti-cancer compositions for delivering 5-fluorouracil to cancer tissues in a warm blooded animal, which compositions contain a 5-fluorouracil in a smaller proportion than conventional compositions but achieve much higher anti-cancer effects with lower toxicity. The present invention also includes the method of treating a cancer sensitive to 5-fluorouracil therapy in a warm-blooded animal by delivering 5-fluorouracil to such cancer in such animal by administering to the animal a therapeutically effective amount of the composition of the present invention. The present invention is thus an improvement over the invention described in our earlier U.S. patent application Ser. No. 15,161 of Feb. 26, 1979, the entire disclosure of which is hereby incorporated by reference for the teachings of the anti-cancer compositions and methods of treatment disclosed therein.

More specifically, this invention provides compositions for delivering 5-fluorouracil to cancer tissues in a warm-blooded animal, wherein the cancer is a cancer sensitive to 5-fluorouracil, the compositions comprising uracil or salt thereof, and at least one 5-fluorouracil selected from among compounds represented by the formula

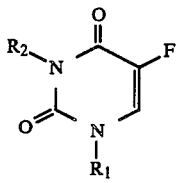

wherein $R_1$ and $R_2$ are the same or different and are each a hydrogen atom, tetrahydrofuryl, $C_2$–$C_{12}$ alkoxymethyl or $C_2$–$C_{12}$ alkylcarbamoyl, in a small amount of less than 0.1 mole per mole of the uracil or salt thereof.

DETAILED DESCRIPTION OF THE INVENTION

Salts of uracil which are useful for the present invention are those that are pharmacologically acceptable. Typical of such salts are alkali metal salts, especially the sodium salt and the potassium salt of uracil.

The 5-fluorouracils useful for the present invention are those represented by the formula (I).

1,3-bis(2-tetrahydrofuryl)-5-fluorouracil (Compound 1)
3-(2-tetrahydrofuryl)-5-fluorouracil (Compound 2)

Compounds 1 and 2 given above are prepared by known processes. For example, processes are disclosed in Published Unexamined Japanese Patent Application No. 50384/1975 for Compound 1, and in Published Unexamined Japanese Patent Application No. 68189/1977 for Compound 2.

For the preparation of the anti-cancer composition of this invention, the ratio of uracil or a salt thereof to the 5-fluorouracil varies with the kinds of the uracil salts and of the 5-fluorouracil compounds. Generally the 5-fluorouracil should be used in a very small amount of less than 0.1 mole pr mole of the uracil or salt thereof. Usually it is preferable to use at least 0.01 mole to less than 0.1 mole, more preferably up to 0.09 mole, of the 5-fluorouracil per mole of the uracil or salt thereof.

When the 5-fluorouracil is admixed with uracil or a salt thereof in a very small amount of less than 0.1 mole per mole of the uracil or salt thereof according to the present invention, the uracil or salt thereof enables the 5-fluorouracil to produce a remarkably enhanced anti-cancer effect than when the 5-fluorouracil is used in larger amounts. Therefore, the 5-fluorouracil, which is the active component of the present composition, can be given at a reduced dose. Additionally the composition of this invention has the outstanding advantage that when tested in animals for toxicity in terms of variations in the body weight, the composition exhibits lower toxicity with a decrease in the dose of the 5-fluorouracil.

The anti-cancer compositions of this invention comprising a 5-fluorouracil and uracil or a salt thereof are useful for curing cancers in warm-blooded animals. When the 5-fluorouracil component (i.e., a derivative of 5-fluorouracil) is converted to 5-fluorouracil per se in vivo, the presence of the uracil or salt thereof suppresses the decomposition and inactivation of the resulting 5-fluorouracil, consequently permitting the composition to produce an outstanding anti-cancer effect.

The 5-fluorouracil functions in the manner of a prodrug. That is, the 5-fluorouracil, selected from compounds 1 and 2 in the composition of the present invention will be converted in the body to 5-fluorouracil. The concentration of 5-fluorouracil maintained in the cancer cellular tissue of test animals will be maintained for an extended period of time. The composition of the present invention thus functions as a delivery system for delivering 5-fluorouracil to a tumor in a patient. The tumors which respond to the present treatment are those tumors which are sensitive to 5-fluorouracil therapy. Thus cancers sensitive to 5-fluorouracil therapy are treated by administering to a patient having such cancer an effective amount of the composition of the present invention. As known to those in the art, the cancers which are sensitive to 5-fluorouracil therapy include breast cancer, cancer of the esophagus, lung cancer, liver cancer and cancers of the gastro-intestinal system, such as stomach cancer, cancers of the intestines, cancer of the rectum, and the like.

With the present invention, uracil or a salt thereof and a 5-fluorouracil can be mixed together in the form of a preparation for administration, or can be given individually. According to therapeutic purposes, the anti-cancer composition of this invention can be given in the form of various preparations, such as tablets, capsules, granules, etc., for oral administration, and injection solutions, suppositories, etc., for non-oral administration.

These preparations are formulated by usual methods using excipients or carriers heretofore used in the art. The amount of the 5-fluorouracil to be contained in the tablet, capsule, suppository or like administration unit, although variable with the 5-fluorouracil employed and the other uracil component and not particularly limited, is usually about 1 to about 100 mg for oral administration, about 1 to about 250 mg for injection and about 5 to about 400 mg for suppositories. It is desirable that the present composition be given at a daily dose, calculated as the 5-fluorouracil, of about 1 to about 400 mg for oral administration, about 1 to about 1000 mg for injection and about 5 to about 1000 mg as suppositories, although the dose varies with the kinds of the uracil components.

The anti-cancer compositions of this invention have an exceedingly higher anti-cancer effect than those containing a 5-fluorouracil alone or in larger amounts, and can therefore be administered at smaller doses. As will be apparent from the anti-cancer effects tables below, the same anti-cancer effect can be achieved by the composition of this invention when it is used in about 1/5 to about 1/10 the amount needed for those containing the 5-fluorouracil alone, and in about ½, or less than ½, the amount needed for those containing the 5-fluorouracil in larger quantities together with uracil. Thus the present composition has a remarkable advantage

EXAMPLES OF THE INVENTION

Typical of anti-cancer compositions of the invention are given below.

| Preparation 1 | |
|---|---|
| Compound 1 | 50 mg |
| Uracil | 450 mg |
| Lactose | 62 mg |
| Magnesium stearate | 18 mg |
| Talc | 8 mg |
| Hydroxypropylmethyl cellulose | 12 mg |
| Per tablet | 600 mg |

Tablets are formulated from the above ingredients in the proportions given.

| Preparation 2 | |
|---|---|
| Compound 2 | 20 mg |
| Uracil | 450 mg |
| Lactose | 172 mg |
| Magnesium stearate | 58 mg |
| Per capsule | 700 mg |

An encapsulated preparation is formulated from the above ingredients in the proportions given.

| Preparations 3 | |
|---|---|
| Compound 1 | 150 mg |
| Sodium salt of uracil | 900 mg |
| Witepsol W-35 | 950 mg |
| Per suppository | 2000 mg |

Suppositories are prepared from the above ingredients in the proportions given.

The anti-cancer effect of compositions of this invention will be described below with reference to the following experimental example.

Experimental Example

Compositions of this invention are tested for anti-cancer effect on sarcoma 180 and AH 130, using mice of ICR strain and rats of Donryu strain, respectively, with 6 animals in each group. Cancer cells in an amount of $10^6$ cells are subcutaneously transplanted in the back area of each animal. Twenty-four hours after the transplant, a composition prepared by dissolving or suspending a 5-fluorouracil and uracil in 5% aqueous solution of gum arabic in proportions listed below is orally given to each animal once daily for 7 consecutive days. On the 10th day after the transplant, each tumor is removed and weighed. The cancer inhibition ratio is calculated from the ratio of the average tumor weight of each test group to that of the control group. On the other hand, the average body weight of each test group is determined before the transplant and after the removal of tumor, in comparison with that of the control group, to indicate the toxicity of the composition in terms of the increase in the average body weight. The animals of the control group is treated in the same manner as above except that no composition is given. Tables 1 and 2 show the result.

TABLE 1

Anti-cancer effect of Compound 1 admixed with uracil

| Amount of Compound 1 per mole of uracil (mole) | Dose of Comp. 1 (mg/kg) | Effect on sarcoma 180 | | Effect on AH 130 | |
|---|---|---|---|---|---|
| | | Inhibition ratio (%) | Gain in average body weight (g) | Inhibition ratio (%) | Gain in average body weight (g) |
| Comparison | | | | | |
| Compound 1 only | 150 | 68 | 1.8 | 67 | 15 |
| | 100 | 60 | 1.8 | 53 | 33 |
| | 67 | 38 | 2.0 | 41 | 41 |
| | 44 | 24 | 4.9 | 30 | 43 |
| 0.1 | 32 | 66 | −3.4 | 78 | 2 |
| | 16 | 42 | 1.0 | 56 | 14 |
| | 8 | 28 | 3.3 | 19 | 26 |
| | 4 | 14 | 4.2 | 12 | 39 |
| Invention | | | | | |
| 0.08 | 16 | 67 | 2.8 | 67 | 24 |
| | 8 | 41 | 3.4 | 29 | 31 |
| 0.04 | 16 | 75 | 2.8 | 76 | 20 |
| | 8 | 53 | 3.6 | 58 | 36 |
| 0.02 | 16 | 81 | 3.1 | 76 | 24 |
| | 8 | 54 | 3.6 | 66 | 33 |
| | 4 | 38 | 4.6 | 33 | 40 |
| 0.015 | 16 | 84 | 2.8 | 83 | 23 |
| | 8 | 53 | 3.9 | 69 | 30 |
| 0.01 | 16 | 71 | 3.3 | 85 | 23 |
| | 8 | 63 | 4.6 | 71 | 43 |
| Control | 0 | — | 5.4 | — | 54 |

TABLE 2

Anti-cancer effect of Compound 2 admixed with uracil

| Amount of Compound 2 per mole of uracil (mole) | Dose of Comp. 2 (mg/kg) | Effect on sarcoma 180 | | Effect on AH 130 | |
|---|---|---|---|---|---|
| | | Inhibition ratio (%) | Gain in average body weight (g) | Inhibition ratio (%) | Gain in average body weight (g) |
| Comparison | | | | | |
| Compound 2 only | 64 | 79 | 0.4 | 89 | −11 |
| | 32 | 41 | 1.5 | 58 | 17 |

TABLE 2-continued

Anti-cancer effect of Compound 2 admixed with uracil

| Amount of Compound 2 per mole of uracil (mole) | Dose of Comp. 2 (mg/kg) | Effect on sarcoma 180 Inhibition ratio (%) | Effect on sarcoma 180 Gain in average body weight (g) | Effect on AH 130 Inhibition ratio (%) | Effect on AH 130 Gain in average body weight (g) |
|---|---|---|---|---|---|
|  | 16 | 33 | 3.2 | 29 | 28 |
|  | 8 | 19 | 4.1 | 13 | 39 |
| 0.1 | 32 | 88 | −3.1 | 81 | −17 |
|  | 16 | 84 | 0.6 | 42 | 11 |
|  | 8 | 40 | 2.6 | 20 | 24 |
| Invention |  |  |  |  |  |
| 0.08 | 16 | 97 | 1.8 | 57 | 23 |
|  | 8 | 56 | 2.8 | 29 | 28 |
| 0.04 | 8 | 71 | 1.9 | 51 | 23 |
|  | 4 | 59 | 3.8 | 29 | 32 |
| 0.02 | 8 | 75 | 2.4 | 49 | 24 |
|  | 4 | 43 | 3.6 | 32 | 33 |
| 0.015 | 8 | 73 | 1.9 | 54 | 20 |
|  | 4 | 39 | 3.8 | 24 | 38 |
| 0.01 | 8 | 74 | 2.3 | 51 | 32 |
|  | 4 | 32 | 4.8 | 20 | 43 |
| Control | 0 | — | 5.0 | — | 43 |

These tables reveal that the anti-cancer compositions of this invention produce exceedingly high effects than when the corresponding 5-fluorouracils are used singly or in larger amounts with uracil than in the present invention. Compound 1 as used in combination with uracil according to the present invention is comparable in anti-cancer effect (inhibition ratio) to the corresponding compound as used singly when the former is given at about 1/10 the dose of the latter. With Compound 2, the dose given according to the present invention is about 1/5 to about ⅛ the dose otherwise needed for producing an equivalent anti-cancer effect. The tables also indicate that a 5-fluorouracil incorporated in the composition of the invention is comparable in anti-cancer effect to the same compound as used with uracil in a higher amount of at least 0.1 per mole of uracil when the former is given at about ½, or less than ½, the dose in the latter case. Stated more specifically with reference to Table 1 for example, the composition containing Compound 1 in a higher proportion of 0.1 mole per mole of uracil achieves inhibition ratios of 66% for sarcoma 180 and 78% for AH 130 when given at a dose of 32 mg/kg calculated as Compound 1. In contrast, the composition containing Compound 1 in a low proportion of 0.01 to 0.08 mole per mole of uracil achieves corresponding inhibition ratios of 67 to 84% and 67 to 85% when given at a dose of 16 mg/kg, i.e., one half the former dose. Further while an inhibition ratio of 68% is achieved by the single use of Compound 1 at a dose of 150 mg/kg, an equivalent effect can be achieved by the present invention with a dose of 16 mg/kg which is about 1/10 of the former. Tables 1 and 2 show that such remarkable effects can be produced according to the present invention. Reference to dosages used herein refers to the amount of the 5-fluorouracil which is administered.

The average body weights of the animals to which compositions of the invention are given are comparable to those of the animals to which the corresponding 5-fluorouracils are administered singly, and involve gains when compared with those of the animals receiving compositions with higher 5-fluorouracil contents. Thus the present compositions are equivalent to or lower than conventional compositions in toxicity.

Although uracil or salts thereof have no anti-cancer effect whatsoever, the use of the combination of uracil or salt thereof and the 5-fluorouracil in combination therewith according to the present invention produces a greatly enhanced anti-cancer effect, with the cancer tissues having a greatly increased concentration of 5-fluorouracil itself, whereas other body tissues, such as the blood serum, exhibit little or no increase in the concentration of 5-fluorouracil. This indicates that the present composition is an ideal therapeutic agent for the treatment of cancer cellular tissue sensitive to 5-fluorouracil therapy.

Briefly the anti-cancer compositions of this invention comprising uracil or a salt thereof, and a 5-fluorouracil in a very small amount enable the 5-fluorouracil to produce an exceedingly higher anti-cancer effect with lower toxicity and at smaller doses than heretofore possible. Determination of concentrations of 5-fluorouracil in the blood and cancer tissues Ascites cells ($5 \times 10^6$) of AH-130 are subcutaneously transplanted in the armpit portion of male rats of Donryu strain weighing about 200 g. Seven days thereafter, the rats with cancer cells weighing at least 2 g are used, five rats in each group.

An anti-cancer composition comprising a 5-fluorouracil (a) alone or in combination with uracil (b) in the proportion(s) listed in Table 3 is suspended in a 5% solution of gum arabic immediately before use, and the suspension is orally given to the animal at the listed dose. One, two, four and eight hours after the administration, the blood serum and cancer tissue homogenate are collected, each of which is acidified with hydrochloric acid and extracted with chloroform. The resulting aqueous layer is examined for antibiotic activity according to the thin-cup method (Media Circle, Vol. 92, p. 259, 1967) with use of *Staphylococcus aureus* 209P strain. The results are given in Table 3 in terms of 5-fluorouracil concentration.

We claim:

1. Anti-cancer composition for delivering 5-fluorouracil to cancer tissues in a warm-blooded animal, wherein the cancer is a cancer sensitive to 5-fluorouracil, said composition comprising uracil or pharmaceutically acceptable salt thereof and a 5-fluorouracil pro drug selected from the group consisting of 1,3-bis(2-tetrahydrofuryl)-5-fluorouracil and 3-(2-tetrahydrofuryl)-5-fluorouracil in a small amount of about 0.01 to less than 0.1 mole per mole of the uracil or salt thereof.

2. An anti-cancer composition as defined in claim 1 wherein the salt of uracil is an alkali metal salt.

3. An anti-cancer composition as defined in claim 2 wherein the alkali metal salt is sodium or potassium salt.

4. An anti-cancer composition as defined in claim 1 wherein 0.01 to 0.09 mole of the 5-fluorouracil is used per mole of the uracil or salt thereof.

5. An anti-cancer composition as defined in claim 1 which is an oral preparation.

6. An anti-cancer composition as defined in claim 1 which is an injection preparation.

7. An anti-cancer composition as defined in claim 1 which is a suppository.

8. A method of delivering 5-fluorouracil to a cancer sensitive to 5-fluorouracil in a warm-blooded animal, said method comprising administering to the animal the anti-cancer composition of claim 12 in the form of a single preparation in an amount which is effective to deliver an anti-cancer effective amount of 5-fluorouracil to the cancer.

9. A method of delivering 5-fluorouracil to a cancer sensitive to 5-fluorouracil in a warm-blooded animal, the method comprising administering to the animal in separate doses uracil or a pharmaceutically acceptable salt thereof and a 5-fluorouracil pro drug selected from the group consisting of 1,3-bis(2-tetrahydrofuryl)-5-fluorouracil and 3-(2-tetrahydrofuryl)-5-fluorouracil, wherein about 0.01 to less than 0.1 mole of said pro drug is used per mole of the uracil or salt thereof, in an amount which is effective to deliver an anti-cancer amount of 5-fluorouracil to the cancer.

* * * * *